(12) United States Patent
Merchant (10) Patent No.: US 8,221,352 B2
(45) Date of Patent: Jul. 17, 2012

(54) DISPOSABLE SAFETY NEEDLE SYSTEM AND SAFETY ENCLOSURE MEANS

(76) Inventor: Michael Merchant, Franklin, MA (US)

(*) Notice: Subject to any disclaimer, the term of this patent is extended or adjusted under 35 U.S.C. 154(b) by 80 days.

(21) Appl. No.: 12/697,148

(22) Filed: Jan. 29, 2010

(65) Prior Publication Data

US 2011/0125056 A1  May 26, 2011

Related U.S. Application Data

(60) Provisional application No. 61/206,333, filed on Jan. 29, 2009.

(51) Int. Cl.
*A61M 5/00* (2006.01)
(52) U.S. Cl. .................. 604/110; 604/164.08; 604/192; 604/263
(58) Field of Classification Search ............ 604/110, 604/192, 198, 199, 263, 268, 162, 164.08
See application file for complete search history.

(56) References Cited

U.S. PATENT DOCUMENTS

| 5,395,347 A * | 3/1995 | Blecher et al. ............... 604/198 |
| 2005/0137528 A1 * | 6/2005 | Wilkinson ..................... 604/110 |

* cited by examiner

*Primary Examiner* — Bhisma Mehta
(74) *Attorney, Agent, or Firm* — Chapin IP Law, LLC (57) ABSTRACT

Techniques disclosed herein include a disposable safety needle assembly and safety enclosure for internally shielding a used or contaminated needle. The needle assembly has a needle cannula slidably disposed within a safety enclosure. The safety enclosure includes an internally disposed flexible safety member. The flexible safety member has face portion transversely situated and having a safety feature disposed to the needle and that slides thereon. Retracting the needle within the safety enclosure to a point wherein the sharp tip of the needle is beyond the needle protection section of the flexible member causes the protection section to travel transversely to the direction of motion of the needle. As a result, the safety feature receives the sharp tip of the needle and prevents the needle from exiting the enclosure, thereby maintaining the needle safely after use.

20 Claims, 6 Drawing Sheets

DISPOSABLE SAFETY NEEDLE SYSTEM AND SAFETY ENCLOSURE MEANS

CROSS REFERENCE TO RELATED APPLICATIONS

This application is a Non-Provisional utility patent application claiming priority to U.S. Provisional Patent application Ser. No. 61/206,333 filed Jan. 29, 2009 and is incorporated herein by reference.

BACKGROUND OF THE INVENTION

1. Field of the Invention

This invention generally relates generally to medical safety devices and in particular to a disposable safety needle having an enclosure means.

2. Description of the Related Art

Fluid collection sets, catheters, and intravenous infusion sets are typically used to collect bodily fluids from a patient or to infuse liquids into a patient. These devices typically include a length of flexible plastic tubing with a proximal end connected to a plastic fitting and a distal end connected to a needle, or in the case of a catheter, a tubular assembly. In practice, fluid is transferred via the plastic tubing either to or from the needle or tubular assembly.

Accidental sticks with a needle cannula can be not only painful but can also transmit disease from a patient to medical personnel. Similarly, catheters may retain fluids when they are removed from a patient and transmit disease via these fluids if passed to medical personnel. As a result, nearly all needle assemblies and other sharp medical implements are employed with an apparatus for enclosing the sharp tip of the needle or tubular assembly both prior to and after use.

Protection prior to use is typically achieved by a rigid plastic tube that surrounds a portion of the needle including the sharp edge. This rigid tube typically has a proximal end frictionally mounted to or near the hub and a distal end that extends beyond the distal end of the piercing element. The rigid tube itself surrounds the needle and prevents contact with the needle point until it is removed. Once removed, the plastic tube is discarded immediately prior to use of the piercing element.

One prior art form of protecting the needle after use is the use of a tubular shield that can be telescoped relative to both the hub and piercing element from a proximal position where the piercing element is exposed to a distal position where the piercing element is safely within the tubular shield. Shields of this type typically include means for releasably holding the shield in its proximal position and for holding the shield more securely in its distal position. Some devices include a spring for generating relative movement between the shield and the piercing element. In some instances the piercing element is withdrawn proximally into the shield.

However, this prior art method requires movement of the hands of the medical provider toward the exposed needle and therefore may allow needle stick injuries during the recapping.

IN addition, a small volume of blood or other bodily fluid may remain in or on a piercing element after the piercing element has been withdrawn from the patient or when a catheter is removed from a patient. This residual fluid may splatter as the piercing element is retracted rearward into the prior art shield. In general, the larger the bore of the needle, the larger the acceleration of the needle in the proximal direction, and any transverse acceleration may result in the splatter of the residual bodily fluid.

The prior art has worked to reduce the likelihood of such splatter. In one example, an indwelling injector needle assembly has the hub slide along an inner periphery of the holder between a first position near the distal end of the holder and a second position near a proximal end of the holder. The latching mechanism is formed in and disposed between the hub and the holder so that the hub is inhibited from moving from the first position toward the second position, and vice versa. The needle edge can be retracted within the holder while remaining fixed to a patient's skin.

However, this form of the prior art has at least one problem. This structure includes a non-rotating needle. As is known in the art, a rotatable needle is preferable to a non-rotatable needle in order to maximize blood or fluid flow to or from a vessel in which the needle is inserted. The prior art device prevents the needle from being rotated after cannulation. The needle and hub cannot rotate relative to the cylindrical holder due to the lug being slidably engaged with the guide groove in the hub. Therefore the needle cannot be rotated when needed after cannulation in order to maximize blood or fluid flow to or from the vessel.

Another prior art device describes a system which provides a snap-on exterior mounted enclosing guard can be added to a needle assembly. A spring forms an essential element of this safety needle assembly. In particular, the spring includes an turned in flange which is described as imperforate, such that it acts as a blocking flange. The enclosing guard, by way of the imperforate blocking flange, upon the withdrawal of the needle from the blood donor or patient, blocks the contaminated needle point.

Thus, this prior art device is limited in its use of materials and design in that the flange must be imperforate in order to prevent the needle tip from coming into contact with any worker. However, the enclosing guard is in proximate relation to and actually touches the needle cannula while it is being withdrawn from the patient. Thus, this assembly can become contaminated itself. Although the needle point is blocked, the system may still contaminate the worker by the blood or fluid which is on the enclosing guard.

Thus, what is needed is a safety needle device that allows for the maximum blood or fluid flow to or from the vessel, and overcomes the limitations of the prior art.

SUMMARY OF THE INVENTION

The present invention addressed the problem of potential worker contamination both by needle stick and accidental exposure without needle stick. A new system and enclosure means is provided which prevents the needle from exiting the enclosure once it has been withdrawn from the patient, shields the needle point and simultaneously isolates the locking member from contact with the worker and any other patient or person in proximity to the patient. In addition, the system and enclosure of the present invention also prevents the medical care giver from accidentally coming in contact with body fluid of the patient.

The needle assembly has a needle cannula which is longitudinally disposed within a safety enclosure and slidably maintained therein. The safety enclosure incorporates an internally disposed flexible member situated along the longitudinal plane, having a needle protection section transversely disposed to the needle cannula and cooperatively sliding thereon. The needle protection section can either be imperforate, in which case a detent is advantageously disposed thereof to capture the tip of the needle cannula, or it can be perforate, in which case the perforation is of a diameter less than the diameter of the cannula such that it can capture and retain the tip of the cannula. Retraction of the needle cannula within the safety enclosure to a point wherein the sharp tip of the needle cannula is beyond the needle protection section of the flexible member causes the protection section to travel transversely to the direction of motion of the needle cannula and block the sharp tip from exiting the enclosure, thereby maintaining the needle safely after use and preventing the accidental exposure with the patient's body fluids.

BRIEF DESCRIPTION OF THE DRAWINGS

Aspects of the present invention are pointed out with particularity in the appended claims. The present invention is illustrated by way of example in the following drawings in which like references indicate similar elements. The following drawings disclose various embodiments of the present invention for purposes of illustration only and are not intended to limit the scope of the invention. For purposes of clarity, not every component may be labeled in every figure. In the figures:

DETAILED DESCRIPTION

The following detailed description sets forth numerous specific details to provide a thorough understanding of the invention. However, those skilled in the art will appreciate that the invention may be practiced without these specific details. In other instances, well-known methods, procedures, components, protocols, processes, and circuits have not been describe in detail so as not to obscure the invention.

Certain terminology may be used in the following description for convenience only and is not limiting. The words "lower" and "upper" and "top" and "bottom" designate directions only and are used in conjunction with such drawings as may be included to fully describe the invention. The terminology includes the above words specifically mentioned, derivatives thereof and words of similar import.

Where a term is provided in the singular, the inventors also contemplate aspects of the invention described by the plural of that term. As used in this specification and in any claims, the singular forms "a", "an", and "the" include plural references unless the context clearly dictates otherwise, e.g. "a derivative work". Thus, for example, a reference to "a method" includes one or more methods, and/or steps of the type described therein and/or which will become apparent to those persons skilled in the art upon reading this disclosure.

Unless defined otherwise, all technical, legal, copyright related and scientific terms used herein have the same meaning or meanings as commonly understood by one of ordinary skill in the art to which this invention belongs. Although any methods and materials similar or equivalent to those described herein can be used in the practice or testing of the present invention, the preferred methods, constructs and materials are described herein. All publications mentioned herein, whether in the text or by way of numerical designation, are incorporated herein by reference in their entirety. Where there are discrepancies in terms and definitions used by reference, the terms used in this application shall have the definitions given herein.

The term "variation" of an invention includes any embodiment of the invention, unless expressly specified otherwise. A reference to "another embodiment" in describing an embodiment does not necessarily imply that the referenced embodiment is mutually exclusive with another embodiment (e.g., an embodiment described before the referenced embodiment), unless expressly specified otherwise.

The terms "include", "includes", "including", "comprising" and variations thereof mean "including but not limited to", unless expressly specified otherwise. The term "consisting of" and variations thereof includes "including and limited to", unless expressly specified otherwise.

The terms "a", "an" and "the" mean "one or more", unless expressly specified otherwise. The term "plurality" means "two or more", unless expressly specified otherwise. The term "herein" means "in this patent application, including anything which may be incorporated by reference", unless expressly specified otherwise. The phrase "at least one of", when such phrase modifies a plurality of things (such as an enumerated list of things) means any combination of one or more of those things, unless expressly specified otherwise.

The phrase "based on" does not mean "based only on", unless expressly specified otherwise. In other words, the phrase "based on" describes both "based only on" and "based at least on". The term "represent" and like terms are not exclusive, unless expressly specified otherwise.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The terms "such as", and/or "e.g." and like terms means "for example", and thus does not limit the term or phrase it explains.

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like. It does not imply certainty or absolute precision, and does not imply that mathematical processing, numerical methods or an algorithm process be used. Therefore "determining" can include estimating, predicting, guessing and the like.

In the embodiments that follow, the safety needle assembly has a needle cannula that is slidably disposed within a safety enclosure. The safety enclosure incorporates an internal safety cover situated along the longitudinal axis of the needle cannula, having a needle protection face section transversely disposed to the needle cannula. The needle protection face section can either be imperforate, in which case a detent is disposed thereon to capture the tip of the needle cannula, or it can be perforate, in which case the perforation through the protection face has a diameter less than the diameter of the needle cannula. In this way, the needle cannula is captured and retained within the safety enclosure.

Figure 1:
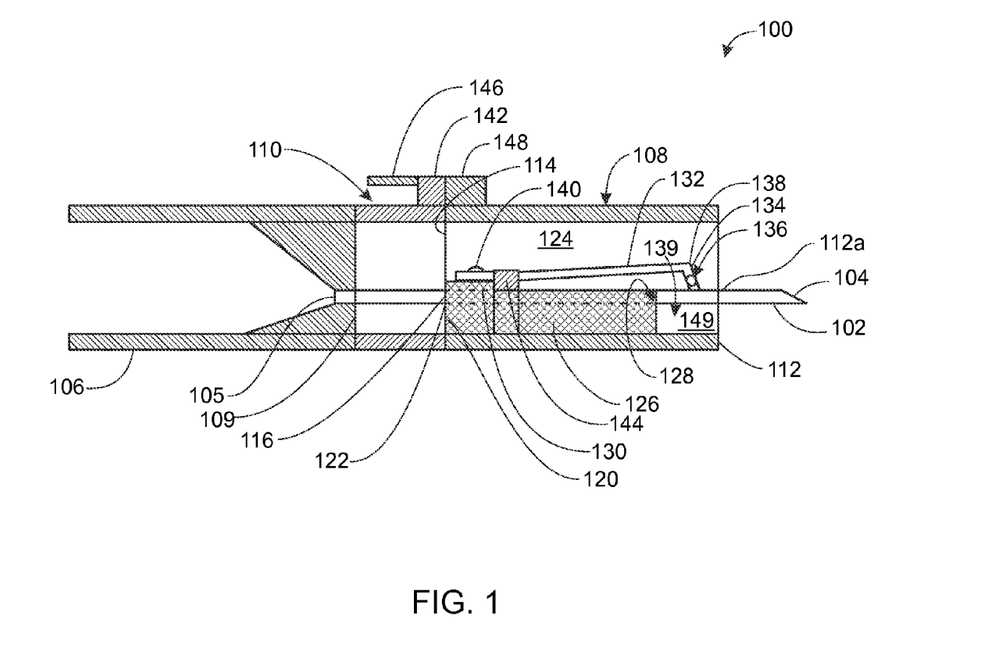
FIG. 1 is a cross sectional view incorporating an embodiment of the present invention in a use position.
Figure 2:
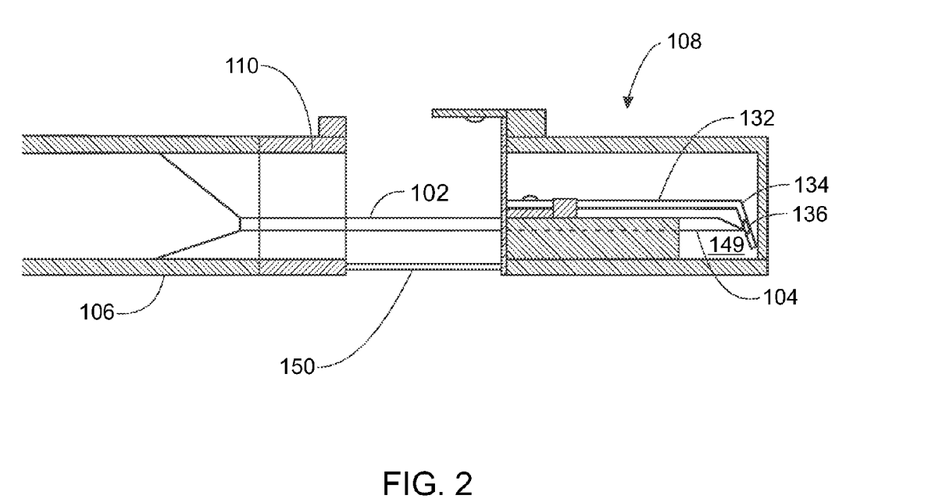
FIG. 2 is a cross sectional view incorporating an embodiment of the present invention the safety position.

With respect to FIGS. 1 and 2, a safety needle assembly 100 is provided that includes a needle cannula 102 suitable for the insertion or removal of fluids to or from a patient. The needle cannula 102 includes a tapered point 104 and a proximal end 105. The proximal end 105 of the needle cannula 102 is attached to a piece of flexible tubing 106 via a connector 109 or through the use of a bonding material as is known in the art.

A safety enclosure 108 includes a forward face 112 having an orifice 112a and a distal end 114 and orifice 116 as well. The orifices 112a and 116 are both sized and configured to allow the tapered point 104 and the body of the needle cannula 102 to slidably pass therethrough. A base portion (hub, hub portion) 110 of the safety needle assembly is secured to the flexible tubing 106. The base portion (hub, hub portion) 110 includes a front face 120 and an orifice 122. Orifice 122 is also sized and configured to allow the body of the needle cannula 102 to pass slidably therethrough.

The safety enclosure 108 includes an interior portion 124 that includes a base portion 126 that extends a portion of the longitudinal length of the safety enclosure 108, but does not extend the entire length. The base portion 126 includes a glide canal 128 into which the needle cannula 102 is disposed within. Thus, the needle cannula 102 is slidably and securely disposed within the safety enclosure 108.

Disposed within the interior portion 124 of the safety enclosure 108 is a first base portion 130 on which a flexible safety cover 132 is disposed. As will be discussed in more detail below, the flexible safety cover 132 includes a face portion 134 that includes a safety feature 136 and in which the face portion 134 is disposed in a generally downward direction by bend 138. The safety cover 132 is biased in a generally downward direction such that so long as the needle cannula 102 is touching the safety cover front face 134, the safety cover 132 will not move. When the needle cannula 102 is moved such that it is no longer touching the front face 134, the safety cover 132 and front face 134 will move in the downward direction shown by arrow 139 and depicted in FIG. 1.

Figure 3:
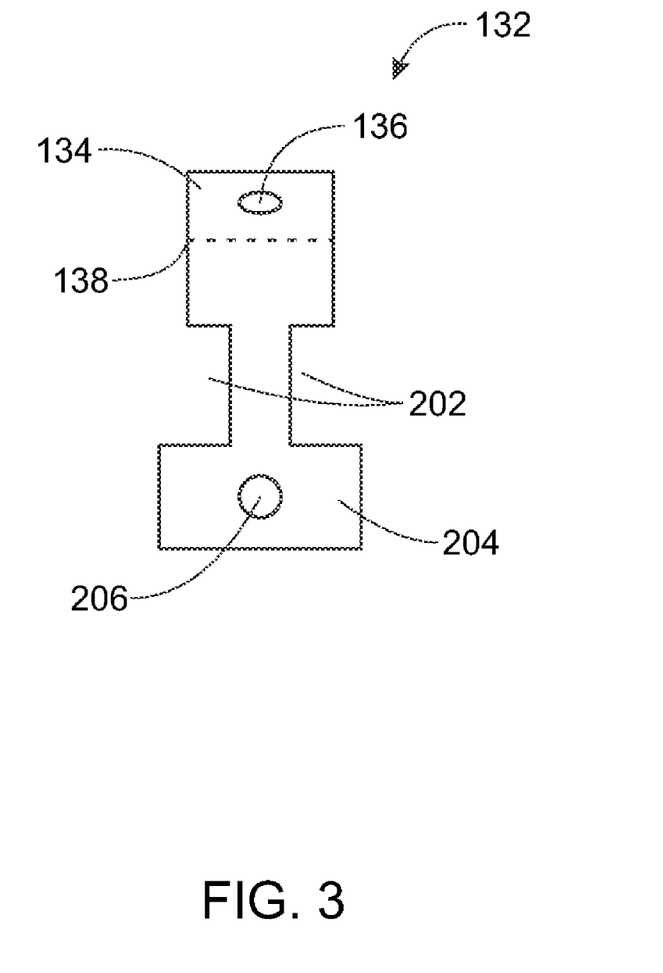
FIG. 3 is top view of the flexible safety member according to an embodiment of the invention located.

The safety cover 132 is depicted in FIG. 3 includes the front face 134, safety feature 136, and first bend 138. In addition, the safety cover 132 further includes notch 202 and rear portion 204. With reference again to FIGS. 1 and 2, the interior portion 124 further includes a second base portion 144. The second base portion 144 is sized and configured to be disposed within notch 202. In this way, movement of the safety cover separate and distinct from the safety enclosure 108 is prevented. The safety cover 132 is affixed to the first base portion 130 via the cooperating post 140 and hole 206.

Figure 4:
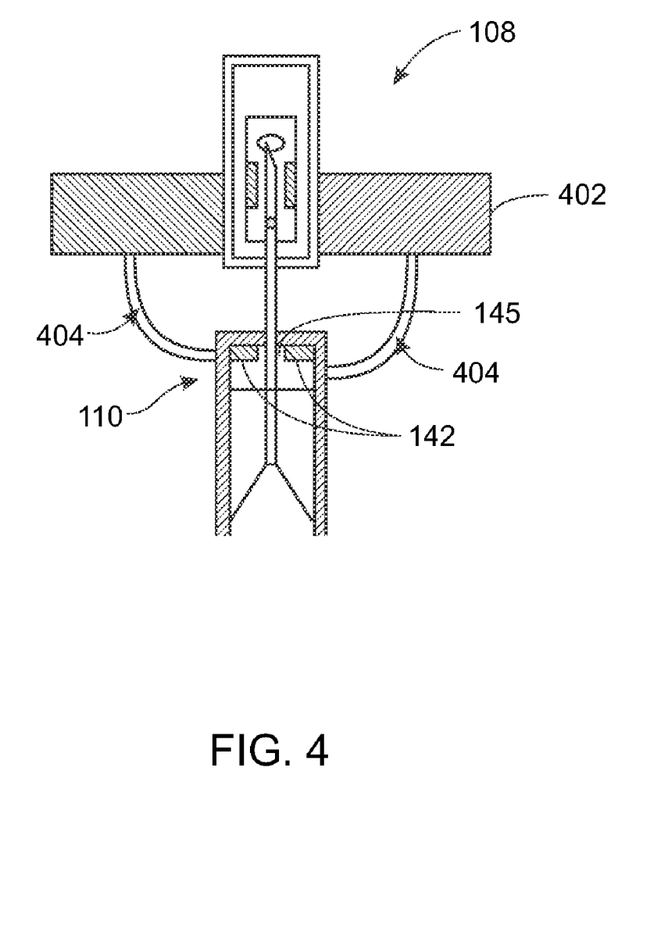
FIG. 4 is a top view of an apparatus incorporating an embodiment of the present invention.

As depicted in FIG. 1, the needle cannula is shown in its extended configuration in which it is to be used to insert or remove fluids from a patient. In this configuration, the safety enclosure 108 is removably secured to the base portion (hub, hub portion) 110 via a hooking mechanism described below. As depicted in FIGS. 1, 2, and 4 the base portion (hub, hub portion) 110 includes a pair of posts 142 having a notch 145 disposed therebetween. The safety enclosure 108 includes a hook portion 146 (or latch 146) that extends longitudinally from the top surface 148 of the safety enclosure 108 that is sized and configured to cooperate with posts 142 and notch 145 to securely and yet removably secure the safety enclosure 108 to base portion (hub, hub portion) 110. The hook portion 146 latches with the notch 145 to prevent any motion of safety enclosure 108, thus preventing the accidental uncovering of the needle cannula 102. The hook portion 146 is also sized and configured to allow a medical care giver to use the present invention in a one-handed operation. By unlatching the hook 146 and sliding the safety enclosure to cover the needle tip (tapered point) 104 using the same hand, the danger of accidently contacting the needle tip 104 is greatly reduced.

In the configuration depicted in FIG. 1, the needle cannula 102 is preventing the downward motion of the front face 134. In this configuration, the needle cannula 102 is extended beyond the front face 134 of the safety enclosure 108 and is ready for use. As can be seen, interior area 149 within the safety enclosure 108 is sized and configured to receive the front face 134 of the safety cover 132.

Figure 5:
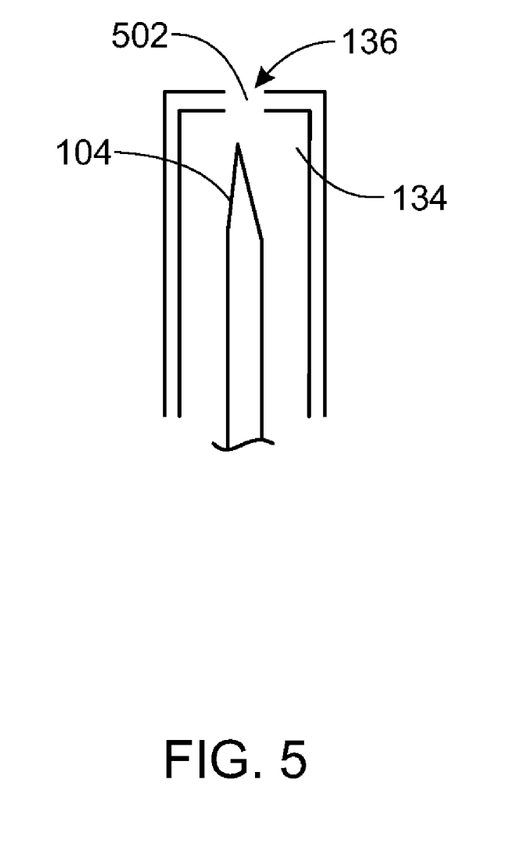
FIG. 5 is cross sectional view of a first embodiment of the safety feature of the present invention.
Figure 6:
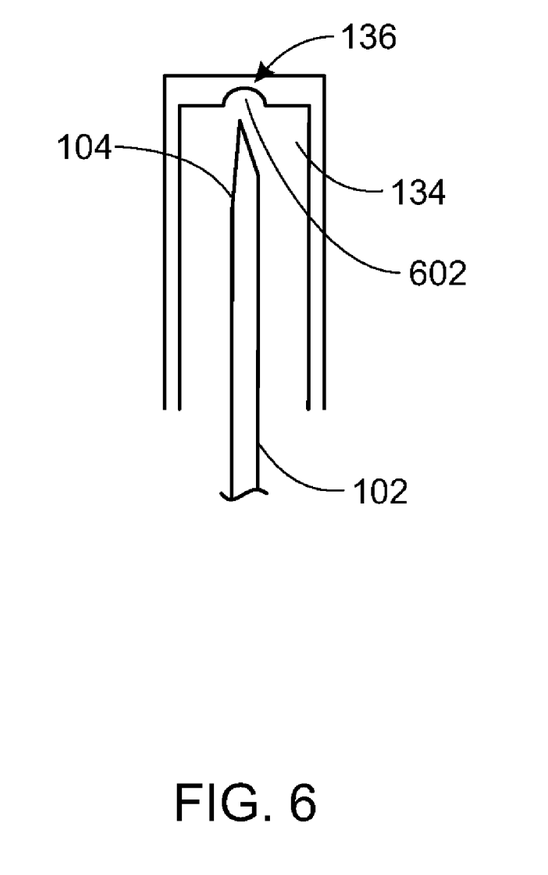
FIG. 6 is a cross sectional view of a second embodiment of the safety feature of the present invention.

As depicted in FIGS. 2 and 4, the needle cannula 102 has been withdrawn into the safety enclosure 108 and the safety cover 132 is now free to move laterally such that the front face 134 is disposed in front of the tapered point 104. In addition, the hub portion (base portion, hub) 110 and safety enclosure 108 are prevented from moving beyond a suitable length by flexible member 150 that is attached to both the hub (hub portion, base portion) 110 and safety enclosure 108. Flexible member 150 is also known as flexible coupling 150 or extensible retainer 150. In addition, as depicted in FIG. 4, flexible wings 402 may be attached to the safety enclosure 108 to allow easier use by medical personnel that may bend the wings 402 upward to facilitate grasping the safety enclosure 108 and then used to provided a surface for taping the safety enclosure 108 to a patient's skin to secure the needle cannula 102 within the patient. In addition, to prevent the safety enclosure 108 from traveling too far and sliding off the end of the needle tip 104, a pair of flexible tethers 404 may be coupled to the base portion (hub, hub portion) 110 and the safety enclosure 108 or the flexible wings 402. These flexible tethers 404 comprise the flexible coupling. As further shown in FIGS. 5 and 6, the tapered point 104 is received in the safety feature 136. In one embodiment, the safety cover 132 is imperforate and the front face 134 includes a detent 602 that is sized configured to receive the tapered point 104 of needle cannula 102 and prevent its movement within the safety enclosure 108. In another embodiment, the safety cover 132 is perforate and front face 134 includes an orifice 502 that is sized and configured to receive only the tip of the tapered point 104 and thereby prevents movement of the needle cannula 102 within the safety enclosure 108. In either embodiment, since the safety cover 132 is internal to the safety housing 108, any fluid which contacts it while it is traveling along the length of the cannula will be maintained within the enclosure.

Once enclosed, the practitioner and others are shielded from any accidental stabs from the tapered point 104. Similarly, since the safety cover 132 is internal to the safety enclosure 108, any fluid which contacts it while it is traveling along the length of the needle cannula 102 will be maintained within the safety enclosure 108. However, this shielding function would be frustrated if the proximal end of the safety enclosure 108 was capable of moving distally beyond the distal end of the needle cannula 102, i.e., past the sharp point. The extensible retainer 150 connects the safety enclosure 108 to the hub 110. As the safety enclosure 108 moves distally along the needle cannula 102, the extensible retainer 150 extends up to, but not beyond, a predetermined length. The extensible retainer 150 thus provides an extensible length beyond which the safety enclosure 108 may not distally extend.

The needle cannula 102 may be any form of needle cannula suitable for a particular usage. For example, the needle cannula 102 may be a Quincke type spinal needle having a gauge in the range from about 12 to 27 and in lengths from about 1" to 7", or the needle cannula 102 may be a Whitacre type spinal having a gauge from about 22 to 27 lengths from about 3½" to 5". Of course, other types of spinal needles could be used.

The needle cannula 102 may also be an epidural needle having a gauge of about 17 to 22 and 2 to 3 inches in length. The needle cannula 102 may also be a fistula needle for dialysis or a blood drawing needle in a blood drawing device as well. These needle cannulas 102 are exemplary only, and it will be understood that the present invention is not limited to a particular needle gauge, type or length.

As discussed above, the needle cannula 102 has a proximal end 105 fixed to the base portion (hub, hub portion) 110, and a distal end that terminates at a sharp tapered point 104. It will be appreciated that the distal end does not necessarily have to terminate at a sharp tapered point 104, and the distal end may have a blunt tip, for instance for use in catheters. The base portion (hub, hub portion) 110 may be any suitable device known in the art, and may have flanges adapted to mate with a locking luer collar, for example. Other types of base portion (hub, hub portion) 110 are possible, such as providing a screw cap adapted to screw onto a corresponding male member of a medical device, which may be a syringe, catheter, etc. Alternatively, the base portion (hub, hub portion) 110 may be the base of a syringe to which the needle assembly is permanently attached. Any method known in the art may be used to fix the hub (hub portion, base portion) onto the proximal end of the cannula, such as adhesives, welding, mechanical engagement or the like.

The safety housing 108 may be sized and configured for various usages. For example, the safety cover 108 may be substantially rectangular in shape, and made of plastic, metal or any other sufficiently tough material that can resist puncturing by the point of the cannula. The safety housing 108 has an outer surface, which may be either smooth or provided with a roughened surface to provide a gripping surface for the user. The housing also may have a down-clip member that may be used to permit gripping and placement of the system by the user. In particular, the down-clip member may be employed to effectuate such action rather than using the wings or flanges, which may not provide the same positive gripping surface and control as use of the down-clip member.

In addition, although the outer surface of the safety housing 108 is preferentially solid, it will be appreciated that the outer surface may also have openings, such as holes, slits, or the like to reduce on material costs, but that any such opening should not permit access to the bodily fluid or permit escape of that fluid. For purposes of this disclosure, such a configuration is still considered to cover that portion of the cannula over which such the safety housing 108 is disposed.

It should be appreciated that other variations to and modifications of the above-described apparatus for protecting a needle cannula may be made without departing from the inventive concepts described herein. Accordingly, the invention should not be viewed as limited except by the scope and spirit of the appended claims.

One embodiment can include an apparatus for securing and protecting the tip of a needle, the needle having a body portion and a diameter, the apparatus comprising: a safety enclosure having an interior space, a first base, a pair of second bases, a longitudinal axis, the needle being slidably disposed within the interior space of the safety enclosure; a base portion; a flexible member having a length, the base portion being flexibly connected to the safety enclosure by the flexible member; a flexible safety member having a face portion, a bendable portion, first and second notches, and rear portion, the flexible safety member being disposed substantially longitudinally within the interior space wherein the rear portion is firmly attached to the first and second notches are sized and configured to receive the pair of second bases, the bendable portion being bent such that the face portion is disposed substantially transversely within the interior space, wherein the bent portion biases the face portion in the transverse direction; the face portion including a safety feature sized and dimensioned to receive the tip of the needle; the safety enclosure having two positions, a use position and a safe position; the use position in which the tip of the needle extends beyond the interior of the safety enclosure and the face portion is prevented from movement by the needle; the safe position in which the safety enclosure is moved such that the tip of the needle is brought into the interior of the safety enclosure to a safe position where the tip of the needle is brought further into the interior than the face portion of the flexible safety member, wherein the face portion is able to move transversely and to cover the tip of the needle, wherein the tip of the needle is received by the safety feature.

The safety feature can comprise an orifice in the face portion of the flexible safety member that is sized and dimensioned to receive the tip of the needle. The orifice of the safety feature can have a diameter that is less than the diameter of the needle body. The flexible safety member can be constructed of material that has sufficient strength to prevent the tip of the needle from further expanding the diameter of the orifice of the safety feature. The safety feature can comprise an indent in the face portion of the flexible safety member that is sized and dimensioned to receive the tip of the needle. The indent of the safety feature has a diameter that is less than the diameter of the needle body. The flexible safety member can be constructed of material that has sufficient strength to prevent the tip of the needle from further expanding the diameter of the orifice of the safety feature. The safety enclosure can be substantially a rectangular parallelepiped in shape. The rectangular parallelepiped can be a rectangular cuboid. The safety enclosure can be substantially cylindrical in shape. The safety enclosure can be constructed of a material having sufficient strength to resist being punctured by the tip of the needle. The apparatus can further include a piece of hollow tubing having an outer surface, the hollow tubing being mechanically attached to the needle to be in fluid communication with the tip of the needle, the base portion being fixedly disposed about the outer surface of the hollow tubing. The hollow tubing can be flexible. The apparatus can further include a piece of hollow tubing having an outer surface, the hollow tubing being bonded to the needle to be in fluid communication with the tip of the needle, the base portion being fixedly disposed about the outer surface of the hollow tubing. The hollow tubing can be flexible. The apparatus can further include a flexible coupling having a predetermined length, the flexible coupling having two ends, one end being coupled to the base portion and the second end being coupled to the safety enclosure. The flexible coupling can comprise first and second flexible tethers, each of the first and second flexible tethers being coupled between the base portion and the safety enclosure.

Another embodiment includes an apparatus for securing and protecting the tip of a needle, the apparatus comprising: a needle having a body portion and a diameter; a safety enclosure having an interior space, a first base, a pair of second bases, a longitudinal axis, the needle being slidably disposed within the interior space of the safety enclosure; a base portion; a flexible member having a length, the base portion being flexibly connected to the safety enclosure by the flexible member; a flexible safety member having a face portion, a bendable portion, first and second notches, and rear portion, the flexible safety member being disposed substantially longitudinally within the interior space wherein the rear portion is firmly attached to the first and second notches are sized and configured to receive the pair of second bases, the bendable portion being bent such that the face portion is disposed substantially transversely within the interior space, wherein the bent portion biases the face portion in the transverse direction; the face portion including a safety feature sized and dimensioned to receive the tip of the needle; the safety enclosure having two positions, a use position and a safe position; the use position in which the tip of the needle extends beyond the interior of the safety enclosure and the face portion is prevented from movement by the needle; the safe position in which the safety enclosure is moved such that the tip of the needle is brought into the interior of the safety enclosure to a safe position where the tip of the needle is brought further into the interior than the face portion of the flexible safety member, wherein the face portion is able to move transversely and to cover the tip of the needle, wherein the tip of the needle is received by the safety feature. The needle can be a fistula needle, whereby the fistula needle may be used for dialysis. The needle can be a blood drawing needle, whereby the blood drawing needle may be used for drawing blood from a patient.

What is claimed is:

1. An apparatus for securing and protecting the tip of a needle, the apparatus comprising:
    a needle having a body portion and a diameter and a tip of the needle;
    a safety enclosure having an interior space, a first base, a pair of second bases, and a longitudinal axis, the needle being slidably disposed within said interior space of said safety enclosure;
    a base portion;
    a flexible member having a length, said base portion being flexibly connected to said safety enclosure by said flexible member;
    a flexible safety member having a face portion and rear portion, said flexible safety member being disposed substantially longitudinally within said interior space, said face portion being disposed substantially transversely within said interior space;
    said face portion including a safety feature sized and dimensioned to receive the tip of the needle;
    said safety enclosure having two positions, a use position and a safe position;
    said use position in which the tip of the needle extends beyond the interior space of said safety enclosure and said face portion is prevented from transverse movement by the needle;
    said safe position in which said safety enclosure is moved such that the tip of the needle is brought into said interior space of said safety enclosure to a safe position where the tip of the needle is brought further into the interior space than said face portion of said flexible safety member, wherein said face portion is able to move transversely and to retain the tip of the needle, wherein the tip of the needle is received by the safety feature;
    wherein the safety feature comprises an orifice in said face portion of said flexible safety member that is sized and dimensioned to receive the tip of the needle;
    wherein said orifice of said safety feature has a diameter that is less than the diameter of the needle body; and
    wherein the flexible safety member is constructed of material that has sufficient strength to prevent the tip of the needle from further expanding said diameter of said orifice of said safety feature.

2. The apparatus of claim 1, further comprising:
    a latch that removably couples the safety enclosure to the base portion.

3. The apparatus of claim 1 wherein the safety enclosure is substantially a rectangular parallelepiped in shape, and wherein said rectangular parallelepiped is a rectangular cuboid.

4. The apparatus of claim 1, wherein said safety enclosure is substantially cylindrical in shape.

5. The apparatus of claim 1 wherein said safety enclosure is constructed of a material having sufficient strength to resist being punctured by the tip of the needle.

6. The apparatus of claim 1 further including a piece of hollow tubing having an outer surface, said hollow tubing being mechanically attached to the needle to be in fluid communication with the tip of the needle, said base portion being fixedly disposed about the outer surface of the hollow tubing, and wherein said hollow tubing is flexible.

7. The apparatus of claim 1 further including a piece of hollow tubing having an outer surface, said hollow tubing being bonded to the needle to be in fluid communication with the tip of the needle, said base portion being fixedly disposed about the outer surface of the hollow tubing; wherein said hollow tubing is flexible.

8. The apparatus of claim 1, wherein the flexible member further comprises a flexible coupling having a predetermined length, the flexible coupling having two ends, one end being coupled to the base portion and the second end being coupled to the safety enclosure; wherein the flexible coupling comprises first and second flexible tethers, each of said first and second flexible tethers being coupled between the base portion and the safety enclosure.

9. The apparatus of claim 1, wherein the flexible safety member has a bendable portion, and first and second notches, wherein said rear portion is firmly attached to the safety enclosure, wherein said first and second notches are sized and configured to receive said pair of second bases, wherein said bendable portion biases said face portion in a transverse direction.

10. An apparatus for securing and protecting the tip of a needle, the apparatus comprising:
    a needle having a body portion and a diameter and a tip of the needle;
    a safety enclosure having an interior space, a first base, a pair of second bases, and a longitudinal axis, the needle being slidably disposed within said interior space of said safety enclosure;
    a base portion;
    a flexible member having a length, said base portion being flexibly connected to said safety enclosure by said flexible member;
    a flexible safety member having a face portion and rear portion, said flexible safety member being disposed substantially longitudinally within said interior space, said face portion being disposed substantially transversely within said interior space;
    said face portion including a safety feature sized and dimensioned to receive the tip of the needle;
    said safety enclosure having two positions, a use position and a safe position;
    said use position in which the tip of the needle extends beyond the interior space of said safety enclosure and said face portion is prevented from transverse movement by the needle;
    said safe position in which said safety enclosure is moved such that the tip of the needle is brought into said interior space of said safety enclosure to a safe position where the tip of the needle is brought further into the interior space than said face portion of said flexible safety member, wherein said face portion is able to move transversely and to retain the tip of the needle, wherein the tip of the needle is received by the safety feature;

wherein the safety feature comprises an indent in said face portion of said flexible safety member that is sized and dimensioned to receive the tip of the needle;

wherein said indent of said safety feature has a diameter that is less than the diameter of the needle body; and wherein the flexible safety member is constructed of material that has sufficient strength to prevent the tip of the needle from further expanding said diameter of said indent of said safety feature.

11. An apparatus for securing and protecting a needle tip of a needle cannula, the apparatus comprising:

a needle cannula, the needle cannula being elongated and having a proximal end and a distal end, the distal end having a needle tip that has a tapered point;

a base portion, the base portion attached to the proximal end of the needle cannula;

a safety enclosure slidably disposed around a portion of the needle cannula such that the safety enclosure is enabled to slide along a longitudinal length of the needle cannula from the base portion towards the needle tip, the safety enclosure defining an interior portion;

a flexible safety member disposed within the interior portion of the safety enclosure, the flexible safety member situated along a longitudinal axis of the needle cannula, the flexible safety member having a needle protection section transversely disposed relative to the longitudinal axis of the needle cannula such that the flexible safety member cooperatively slides on the needle cannula when the safety enclosure slides along the needle cannula, the needle protection section defining a perforation having a perforation diameter, the perforation diameter being sized sufficient to receive and retain at least a portion of the needle tip, the perforation diameter also being sized less than a diameter of the needle cannula; and an extensible retainer that connects the safety enclosure to the base portion, the extensible retainer configured such that the extensible retainer permits the safety enclosure to slide along the needle cannula a distance sufficient for the needle protection section of the flexible safety member to pass beyond the needle tip such that the needle protection section travels transversely to the longitudinal axis of the needle cannula and receives the needle tip in the defined perforation, the extensible retainer also configured to prevent the safety enclosure from moving entirely beyond the needle tip.

12. The apparatus of claim 11, further comprising:
a latch that removably couples the safety enclosure to the base portion.

13. The apparatus of claim 12, further comprising:
a pair of flexible wings attached to the safety enclosure that facilitate grasping the safety enclosure.

14. The apparatus of claim 13 wherein the needle cannula is a fistula needle compatible with dialysis use.

15. The apparatus of claim 13 wherein the needle cannula is a blood drawing needle.

16. The apparatus of claim 13, further comprising:
flexible tubing attached to the base portion such that fluids entering the needle cannula via the distal end can continue through the flexible tubing.

17. An apparatus for securing and protecting a needle tip of a needle cannula, the apparatus comprising:

a needle cannula, the needle cannula being elongated and having a proximal end and a distal end, the distal end having a needle tip that has a tapered point;

a base portion, the base portion attached to the proximal end of the needle cannula;

a safety enclosure slidably disposed around a portion of the needle cannula such that the safety enclosure is enabled to slide along a longitudinal length of the needle cannula from the base portion towards the needle tip, the safety enclosure defining an interior portion;

a flexible safety member disposed within the interior portion of the safety enclosure, the flexible safety member situated along a longitudinal axis of the needle cannula, the flexible safety member having a needle protection section transversely disposed relative to the longitudinal axis of the needle cannula such that the flexible safety member cooperatively slides on the needle cannula when the safety enclosure slides along the needle cannula, the needle protection section defining a detent, the detent being sized sufficient to receive and retain at least a portion of the needle tip without permitting passage of the needle cannula entirely through the needle protection section, wherein the detent of the needle protection section has a diameter that is less than a diameter of the needle cannula, wherein the needle protection section is constructed of material that has sufficient strength to prevent the tip of the needle cannula from further expanding the diameter of the detent of the needle protection section; and an extensible retainer that connects the safety enclosure to the base portion, the extensible retainer configured to extend to permit the safety enclosure to slide along the needle cannula a distance sufficient for the needle protection section of the flexible safety member to pass beyond the needle tip such that the needle protection section travels transversely to the longitudinal axis of the needle cannula and receives the needle tip in the defined detent, the extensible retainer also configured to prevent the safety enclosure from moving entirely beyond the needle tip.

18. The apparatus of claim 17, further comprising:
a latch that removably couples the safety enclosure to the base portion.

19. The apparatus of claim 18, further comprising:
a pair of flexible wings attached to the safety enclosure that facilitate grasping the safety enclosure.

20. The apparatus of claim 19, further comprising:
flexible tubing attached to the base portion such that fluids entering the needle cannula via the distal end can continue through the flexible tubing.

* * * * *